United States Patent [19]
DeLue et al.

[11] Patent Number: 4,718,919
[45] Date of Patent: Jan. 12, 1988

[54] FUEL ADDITIVE

[75] Inventors: Norman R. DeLue, Akron, Ohio; William R. Roberts, Wexford, Pa.

[73] Assignee: PPG Industries, Inc., Pittsburgh, Pa.

[21] Appl. No.: 913,892

[22] Filed: Oct. 1, 1986

[51] Int. Cl.$^4$ ............................ C10L 1/18; C10L 1/30
[52] U.S. Cl. ................................................ 44/76; 44/77
[58] Field of Search ................................. 44/63, 76, 77

[56] References Cited

U.S. PATENT DOCUMENTS

| | | | |
|---|---|---|---|
| 2,741,548 | 4/1956 | Darling et al. | 44/63 |
| 2,767,069 | 10/1956 | Fay et al. | 44/63 |
| 2,952,121 | 9/1960 | Mitacek | 60/35.4 |
| 2,961,380 | 11/1960 | Fay et al. | 260/462 |
| 3,032,971 | 5/1962 | Shotton | 60/354 |
| 3,227,196 | 1/1966 | Meehan | 141/9 |
| 3,523,014 | 8/1970 | Degray | 44/76 |
| 3,564,091 | 2/1971 | Degray et al. | 44/76 |
| 3,877,890 | 4/1975 | Maisey et al. | 44/76 |
| 4,003,719 | 1/1977 | McCoy et al. | 44/63 |

OTHER PUBLICATIONS

Biocidal Properties of Anti-Icing Additives for Aircraft Fuels, Neihof et al., Applied and Environmental Microbiology, Apr., 1978, pp. 698–703.

The Control of Micro-Organisms in Aircraft Systems, Hill, Journal of the Institute of Petroleum, vol. 56, No. 549, pp. 138–146 (1970).

Screening of Prospective Biocides for Hydrocarbon Fuels, Rogers et al., Development in Industrial Microbiology, vol. 9, pp. 448–467 (1968).

Evaluating Biocidal Fuel Additives for Intermittent Use in Aircraft Fuel Systems, Elphrick et al., Hydrocarbon Microbiology and Metallic Corrosion, pp. 1–7; also in Biodeterioration of Materials, Ed. Waters and Elphrick, Elsevier Publishing Co. Ltd. 1968, pp. 364–370.

U.S. Borax Service Bulletin, No. 978, Biobar ® JF Fuel Fungicide.

*Primary Examiner*—Jacqueline V. Howard
*Attorney, Agent, or Firm*—Irwin M. Stein; Bruce H. Cottrell

[57] ABSTRACT

An anti-icing and biocidal fuel additive including an ethylene glycol monoalkyl ether such as 2-methoxyethanol, and at least one organoborate compound such as 2,2'-oxybis(4,4,6-trimethyl-1,3,2-dioxaborinane) and 2,2'-(1-methyltrimethylenedioxy)bis-(4-methyl-1,3,2-dioxaborinane) is provided.

10 Claims, No Drawings

FUEL ADDITIVE

This invention relates to a novel hydrocarbon fuel additive composition useful both as a biocide and as a deicer.

BACKGROUND OF THE INVENTION

It is known that microorganisms can grow in aircraft fuel tanks thereby causing problems such as filter blockage and corrosion damage. Biocidal fuel additives have been used to control the growth of such microorganisms. 2-Methoxyethanol is a common fuel additive primarily used to prevent icing within the fuel system but also recognized as having biocidal properties as high usage levels of about 5000 parts per million (ppm). BIOBOR JF ® fuel fungicide (a trademark of U.S. Borox & Chemical Corp.) is reported to be more effective than 2-methoxyethanol (See Hill, E. C., *Journal of the Institute of Petroleum*, 56 (549), 138–146 (1970) and U.S. Pat. No. 3,877,890). While BIOBOR JF ® fuel fungicide (a combination of organoborates) is particularly effective against fungi, e.g., *Cladosporium resinae*, other microorganisms found in fuel systems such as bacteria, e.g., Pseudomonas sp., are not as easily controlled by the combination of organoborates.

SUMMARY OF THE INVENTION

Unexpectedly, it has now been found that the combination of an ethylene glycol monoalkyl ether of the formula $RO(CH_2CH_2O)_nH$ wherein R is a $C_1$ to $C_4$ alkyl and n is a number from 1 to 3, and at least one organoborate compound having from 3 to 25 carbon atoms and having the graphic formula

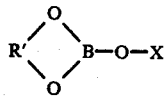

wherein X is selected from the group consisting of hydrogen,

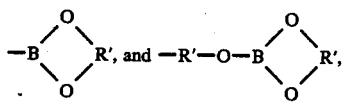

and R' is selected from the group of alpha and beta alkylene radicals having from 3 to 20 carbon atoms, can provide increased effectiveness against bacteria, especially Pseudomonas sp. such as *Pseudomonas aeruginosa*. The present invention thus provides biocidal compositions, such compositions preferably having a weight ratio of from about 10:1 to 1:5 of the ethylene glycol monoalkylether to the organoborate material.

In one embodiment of the invention, the combination of an ethylene glycol monoalkyl ether of the formula $RO(CH_2CH_2O)_nH$ where R and n have their previous significance and a mixture of the organoborate compounds 2,2'-oxybis(4,4,6-trimethyl-1,3,2-dioxaborinane) and 2,2'-(1-methyltrimethylenedioxy)bis-(4-methyl-1,3,2-dioxaborinane), wherein the weight ratio of 2,2'-oxybis(4,4,6-trimethyl-1,3,2-dioxaborinane) to 2,2'-(1-methyltrimethylenedioxy)bis-(4-methyl-1,3,2-dioxaborinane) is from about 2:1 to 3:1, basis total weight of organoborates, and wherein the weight ratio of ethylene glycol monoalkyl ether to organoborates is from about 10:1 to 1:5, can serve as the biocidal composition.

In a particularly preferred embodiment of the invention, a fuel additive composition consists essentially of 2-methoxyethanol, and the organoborates 2,2'-oxybis(4,4,6-trimethyl-1,3,2-dioxaborinane) and 2,2'-(1-methyltrimethylenedioxy)bis-(4-methyl-1,3,2-dioxaborinane) in a weight ratio of 2,2'-oxybis(4,4,6-trimethyl-1,3,2-dioxaborinane) to 2,2'-(1-methyltrimethylenedioxy)bis-(4-methyl-1,3,2-dioxaborinane) of from about 2:1 to 3:1, and a weight ratio of 2-methoxyethanol to organoborates of from about 10:1 to 1:5.

The present invention further provides an improvement in a method of controlling microbial activity in a hydrocarbon fuel system by the addition of a biocidally active component to the fuel, the improvement wherein the biocidally active component includes a mixture of a deicing amount of an ethylene glycol monoalkyl ether of the formula $RO(CH_2CH_2O)_nH$ where R and n have their previous significance, and a biocidal amount of at least one organoborate compound having from 3 to 25 carbon atoms and having the formula

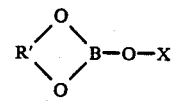

wherein X is selected from the group consisting of hydrogen,

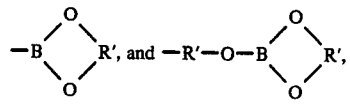

and R' is selected from the group of alpha and beta alkylene radicals having from 3 to 20 carbon atoms, the weight ratio of the ethylene glycol monoalkyl ether to the organoborate compound being from about 10:1 to 1:5.

In one embodiment of the method of controlling deicing and microbial activity in water-containing hydrocarbon fuel, the improvement is the use of a deicing amount of the ethylene glycol monoalkyl ether as previously described and a biocidal amount of the organoborate compounds 2,2'-oxybis(4,4,6-trimethyl-1,3,2-dioxaborinane), and 2,2'-(1-methyltrimethylenedioxy)bis-(4-methyl-1,3,2-dioxaborinane) as the biocidally effective component, the weight ratio of 2,2'-oxybis(4,4,6-trimethyl-1,3,2-dioxaborinane) to 2,2'-(1-methyltrimethylenedioxy)bis-(4-methyl-1,3,2-dioxaborinane) being from about 2:1 to 3:1, and the weight ratio of ethylene glycol monoalkyl ether to organoborates being from 10:1 to 1:5.

DETAILED DESCRIPTION OF THE INVENTION

The present invention concerns a composition including a first component of an ethylene glycol monoalkyl ether of the formula $RO(CH_2CH_2O)_nH$ wherein R is a $C_1$ to $C_4$ alkyl and n is a number from 1 to 3. The ethylene glycol monoalkyl ether of the present invention includes, e.g., ethylene glycol monomethyl ether(2-methoxyethanol), ethylene glycol monoethyl ether(2-ethoxyethanol), ethylene glycol monopropyl ether, ethylene glycol monobutyl ether, diethylene glycol monomethyl ether, triethylene glycol monomethyl ether, diethylene glycol monomethyl ether and triethylene glycol monomethyl ether. Ethylene glycol monomethyl ether or 2-methoxyethanol is particularly preferred as the ethylene glycol monoalkyl ether of this invention.

2-Methoxyethanol is a known fuel additive used to prevent icing of jet engines. Later, the biocidal properties of such a fuel additive were disclosed, (See for example, U.S. Pat. Nos. 3,227,196 and 3,877,890).

The composition of this invention includes as a second component at least one organoborate compound having from 3 to 25 carbon atoms and having the formula

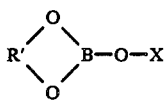

wherein X is selected from the group consisting of hydrogen,

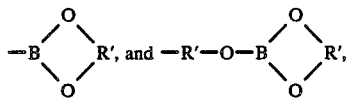

and R' is selected from the group of alpha and beta alkylene radicals having from 3 to 20 carbon atoms. Such organoborate compounds and their preparation from boric acid and glycols are described in U.S. Pat. Nos. 2,741,548 and 2,961,380, and such disclosures of the compounds and their preparation are incorporated herein by reference. Preferred organoborate compounds contemplated by this invention are 2,2'-oxybis(4,4,6-trimethyl-1,3,2-dioxaborinane) and 2,2'-(1-methyltrimethylenedioxy)bis-(4-methyl-1,3,2-dioxaborinane). 2,2'-Oxybis(4,4,6-trimethyl-1,3,2-dioxaborinane) is a borate ester of hexylene glycol and 2,2'-(1-methyltrimethylenedioxy)bis-(4-methyl-1,3,2-dioxaborinane) is a borate ester of 1,3-butylene glycol.

The two above described components are combined as a fuel additive composition which can provide both anti-icing and biocidal properties to hydrocarbon fuel systems, such as jet fuel tanks. The composition of the present invention generally has a weight ratio of the ethylene glycol monoalkyl ether to organoborate material of from about 10:1 to 1:5, more preferably from about 6:1 to about 1:2 and most preferably from about 4:1 to 1:1. In those embodiments including the preferred organoborate compounds, i.e., 2,2'-oxybis(4,4,6-trimethyl-1,3,2-dioxaborinane) and 2,2'-(1-methyltrimethylenedioxy)bis-(4-methyl-1,3,2-dioxaborinane), the weight ratio of such compounds is from about 2:1 to 3:1.

In a method of controlling biocidal activity in water-containing hydrocarbon fuel, the fuel additive composition of this invention is added as a biocidally effective reagent such reagent including a deicing amount of the ethylene glycol monoalkyl ether as previously described and a biocidal amount of the organoborate material as previously described. Such a composition has demonstrated synergistic biocidal properties against bacteria, especially Pseudomonas sp. such as *Pseudomonas aeruginosa* in hydrocarbon fuels. The combination of ethylene glycol monoalkyl ether at levels generally useful only to prevent icing with the organoborates at typical biocidal levels shows greater biocidal properties than either component alone.

The composition of the present invention is added to hydrocarbon fuel, e.g., aircraft fuel, to provide a concentration of about 50 to about 1500 ppm, more preferably about 100 to about 1000 ppm of 2-methoxyethanol, and about 50 to about 1000 ppm, more preferably about 100 to about 500 ppm of the organoborates, e.g., 2,2'-oxybis(4,4,6-trimethyl-1,3,2-dioxaborinane) and 2,2'-(1-methyltrimethylenedioxy)bis-(4-methyl-1,3,2-dioxaborinane).

The hydrocarbon fuel in this invention is any liquid hydrocarbon fuel that is used as a fuel for jet engines. Typically, such fuels contain at least 10 volume percent of normal paraffins boiling in the range of between 32° C. and 288° C., preferably from about 5° C. and 260° C. and having a 90 percent ASTM point of about 243° C. The useful fuels additionally include those fuels meeting military specification MIL-1-27686E.

The water content of the hydrocarbon fuels and hydrocarbon fuel systems is contemplated to generally be from about 100 ppm to about 10,000 ppm or about 0.01 to 1 percent by weight. In fuel systems containing water in excess of these levels, greater amounts of the biocidally effective reagent of this invention may be necessary. By "biocidally effective" is meant the reagent inhibits or controls the growth of those microorganisms generally found within hydrocarbon fuels, especially microorganisms, e.g., Cladosporium sp., Pseudomonas sp., and Candida sp. such as *Cladosporium resinae, Pseudomonas aeruginosa* and *Candida tropicalis*.

The invention is further illustrated by the following examples.

EXAMPLE I

The fuel additive 2-methoxyethanol in combination with a mixture of the organoborates in a weight ratio of 2,2'-oxybis(4,4,6-trimethyl-1,3,2-dioxaborinane) to 2,2'-(1-methyltrimethylenedioxy)bis-(4-methyl-1,3,2-dioxaborinane) of about 2.5:1 was tested as a jet fuel preservative and compared to jet fuel with only the organoborates and a jet fuel control without an additive. The amount of water in the jet fuel, i.e., the fuel to water ratio, was varied to simulate the accumulation of water in a fuel storage system.

A series of four one-liter glass bottles containing 800 milliliters (ml) of No. 2 diesel fuel was prepared for the test with each additive. At the start of each test, all four bottles were inoculated with 2 ml of an adapted mixed inoculum in a Bushnell-Haas medium. The Bushnell-Haas medium is a carbon-free mineral salts solution described in *Journal of Bacteriology*, 41, 653–673 (1941), the description of which is incorporated herein by reference. The microorganisms used in the test were a mixture of: a fungus-*Cladosporium resinae;* a yeast-*Candida tropicalis;* and, a bacterium-*Pseudomonas aeruginosa*. The microorganisms for the inoculate were grown on solid media as described in *SIM Special Publication No. 2, Part* 1, July 1966, and then transferred to Bushnell-Haas medium overlaid with No. 2 diesel fuel. The mixed culture was grown in this environment for one week prior to use so that the mixed inoculum became adapted for growth on diesel fuel hydrocarbons.

The initial fuel to water ratio was 400:1 or 0.25% bottom water. The bottles were stored in the dark for two weeks at 30° Centigrade (°C.). One bottle of each type was then analyzed for microbial content and discarded. The remaining three bottles for each additive and the control were then inoculated with an additional 2 ml of inoculate to bring the fuel to water ratio to 200:1 or 0.50% bottom water. Again, the bottles were stored in the dark for two weeks at 30° C. One bottle of each type was then analyzed for microbial content and discarded. The process was repeated twice more, each time with an additional 2 ml of inoculate for the remaining sample bottles. The results of the test are presented in Table 1. Sample A is the control with no additive, Sample B includes 270 parts per million (ppm) of the organoborates and sample C includes 270 ppm of the organoborates and 1,000 ppm 2-methoxyethanol.

Analysis for the microbial content was by standard dilution and Pour Plate or Spread Plate methods and are expressed in colony forming units per milliliter of sample solution (cfu/ml). *Pseudomonas aeruginosa* bacteria were quantitatively determined by the Pour Plate method using tryptic soy agar media. Although *Candida tropicalis* and *Cladosporium resinae* grow on this media, the rapid growth of *Pseudomonas aeruginosa* allows accurate quantitation.

*Candida tropicalis* yeast was determined by the Pour Plate method using sarbourauds dextrose agar (SDA) containing 0.5 milligram per milliliter (mg/ml) Gentamicin media which inhibits the growth of *Pseudomonas aeruginosa*. *Candida tropicalis* grows more rapidly than *Cladosporium resinae* in this media.

*Cladosporium resinae* yeast was determined by the Spread Plate method using unsupplemented 1.5% agar (Bacto agar) containing 0.1 mg/ml Tellurite as the media. Both *Pseudomonas aeruginosa* and *Candida tropicalis* grow slowly on 1.5% Bacto agar and are inhibited by Tellurite.

TABLE 1

|  | Initial Inocula (cfu/ml) | Microbial Analysis (cfu/ml) | | |
|---|---|---|---|---|
|  |  | Sample A | Sample B | Sample C |
| After 2 Weeks |  |  |  |  |
| bacteria | $6.0 \times 10^5$ | $1.0 \times 10^7$ | $1.0 \times 10^6$ | $2.0 \times 10^4$ |
| yeast | $2.0 \times 10^3$ | $5.5 \times 10^6$ | 10 | 10 |
| fungus | $2.4 \times 10^3$ | $4.0 \times 10^6$ | 10 | 10 |
| After 4 Weeks |  |  |  |  |
| bacteria | $3.0 \times 10^7$ | $5.0 \times 10^6$ | $9.0 \times 10^4$ | 10 |
| yeast | $4.5 \times 10^3$ | $6.5 \times 10^6$ | 10 | 10 |
| fungus | $2.3 \times 10^3$ | $5.0 \times 10^6$ | 10 | 10 |
| After 6 Weeks |  |  |  |  |
| bacteria | $2.5 \times 10^7$ | $1.1 \times 10^7$ | $1.2 \times 10^6$ | $1.0 \times 10^6$ |
| yeast | $7.0 \times 10^2$ | $1.5 \times 10^7$ | 10 | 10 |
| fungus | $4.0 \times 10^2$ | $6.5 \times 10^4$ | 10 | 10 |
| After 8 Weeks |  |  |  |  |
| bacteria | $3.1 \times 10^7$ | $1.8 \times 10^8$ | $7.5 \times 10^6$ | $5.0 \times 10^5$ |
| yeast | $2.5 \times 10^6$ | $1.3 \times 10^7$ | 10 | 10 |
| fungus | $1.0 \times 10^3$ | $6.5 \times 10^5$ | 10 | 10 |

The data in Table 1 indicates that sample B (the organoborates) controlled the fungus and the yeast, but was ineffective in the control of bacteria. However, Sample C (the fuel additive including 2-methoxyethanol, 2,2'-oxybis(4,4,6-trimethyl-1,3,2-dioxaborinane) and 2,2'-(1-methyltrimethylenedioxy)bis-(4-methyl-1,3,2-dioxaborinane) provided greater control of the combination of yeast, bacteria and fungi than the organo borates alone and demonstrated excellent control of bacteria through four weeks or after the initial two additions of inoculate. Thus, the combination of this invention has demonstrated a synergistic effect in the control of microorganisms in hydrocarbon fuel.

Many modifications and variations are possible in light of the present disclosure. It is, therefore, to be understood that the invention may be practiced otherwise than as specifically described and is limited only by the appended claims.

We claim:

1. A hydrocarbon fuel additive composition comprising an ethylene glycol monoalkyl ether of the formula $RO(CH_2CH_2O)_nH$ wherein R is a $C_1$ to $C_4$ alkyl and n is a number from 1 to 3, and at least one organoborate compound having from 3 to 25 carbon atoms and having the formula

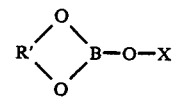

wherein X is selected from the group consisting of hydrogen,

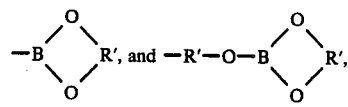

and R' is selected from the group consisting of alpha and beta alkylene radicals having from 3 to 20 carbon atoms, the weight ratio of ethylene glycol monoalkyl ether to organoborate compound in said composition being from 10:1 to 1:5, said ratio also being such that when the composition is added to water-containing hydrocarbon fuel, there is introduced into said fuel from 100 to 1,000 ppm of ethylene glycol monoalkyl ether and from 100 to 500 ppm of organoborate compound.

2. The composition of claim 1 wherein the organoborate compound is a mixture of 2.2'-oxybis(4,4,6-trimethyl-1,3,2-dioxaborinane) and 2,2'-(1-methyltrimethylenedioxy)bis-(4-methyl-1,3,2-dioxaborinane), the weight ratio of 2,2'-oxybis(4,4,6-trimethyl-1,3,2-dioxaborinane) to 2,2'-(1-methyltrimethylenedioxy)bis-(4-methyl-1,3,2-dioxaborinane) being from about 2:1 to 3:1.

3. The composition of claim 1 wherein the ethylene glycol monoalkyl ether is 2-methoxyethanol.

4. A hydrocarbon fuel additive composition consisting essentially of 2-methoxyethanol, and a mixture of the organoborates 2,2'oxybis(4,4,6-trimethyl-1,3,2-dioxaborinane) and 2,2'-(1-methyltrimethylenedioxy)bis-(4-methyl-1,3,2-dioxaborinane), the weight ratio of 2-methoxyethanol to organoborates being from about 10:1 to about 1:5, the weight ratio of 2,2'-oxybis(4,4,6-trimethyl-1,3,2-dioxaborinane) to 2,2'-(1-methyltrimethylenedioxy)bis-(4-methyl-1,3,2-dioxaborinane) being from about 2:1 to 3:1, and said ratio of 2-methoxyethanol to organoborate being such that when the composition is added to water-containing hydrocarbon fuel, there is introduced into said fuel from 100 to 1,000 ppm of 2-methoxyethanol and from 100 to 500 ppm of the organoborate mixture.

5. The composition of claim 4 wherein the weight ratio of 2-methoxyethanol to organoborates is from about 6:1 to 1:2.

6. The composition of claim 4 wherein the weight ratio of 2-methoxyethanol to organoborates is from about 4:1 to 1:1.

7. A method of controlling deicing and microbial activity in a water-containing hydrocarbon fuel, which comprises adding to said hydrocarbon fuel, in combination, from 100 to 1,000 ppm of an ethylene glycol monoalkyl ether of the formula RO(CH$_2$CH$_2$O)$_n$H wherein R is a C$_1$ to C$_4$ alkyl and n is a number from 1 to 3, and from 100 to 500 ppm of at least one organoborate compound having from 3 to 25 carbon atoms, said organoborate compound having the formula:

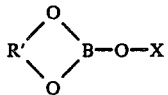

wherein X is selected from the group consisting of hydrogen,

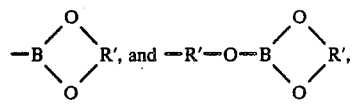

and R' is selected from the group of alpha and beta alkylene radicals having from 3 to 20 carbon atoms, the weight ratio of ethylene glycol monoalkyl ether to organoborate compound in the hydrocarbon fuel being from about 10:1 to 1:5.

8. The method of claim 7 wherein the ethylene glycol monoalkyl ether is 2-methoxyethanol.

9. The method of claim 7 wherein the organoborate material is a mixture of (a) 2,2'-oxybis(4,4,6-trimethyl-1,3,2-dioxaborinane) and (b) 2,2'-(1-methyltrimethylenedioxy)bis-(4-methyl-1,3,2-dioxaborinane), the weight ratio of (a) to (b) being from about 2:1 to 3:1.

10. The method of claim 8 wherein the organoborate material is a mixture of (a) 2,2'-oxybis(4,4,6-trimethyl-1,3,2-dioxaborinane) and (b) 2,2'-(1-methyltrimethylenedioxy)bis-(4-methyl-1,3,2-dioxaborinane), the weight ratio of (a) to (b) being from about 2:1 to 3:1.

* * * * *